US012697296B2

(12) United States Patent
Toressani et al.

(10) Patent No.: US 12,697,296 B2
(45) Date of Patent: Aug. 4, 2026

(54) COSMETIC COMPOSITION FOR THE LIPS

(71) Applicant: L V M H RECHERCHE, Saint-Jean de Brave (FR)

(72) Inventors: Gaelle Toressani, Saint-Jean de Brave (FR); Marine Fabris, Saint-Jean de Brave (FR); Caroline Vilette, Saint-Jean de Brave (FR)

(73) Assignee: L V M H RECHERCHE, Saint-Jean de Brave (FR)

( * ) Notice: Subject to any disclaimer, the term of this patent is extended or adjusted under 35 U.S.C. 154(b) by 467 days.

(21) Appl. No.: 18/005,809

(22) PCT Filed: Jul. 16, 2021

(86) PCT No.: PCT/FR2021/051333
§ 371 (c)(1),
(2) Date: Jan. 17, 2023

(87) PCT Pub. No.: WO2022/103509
PCT Pub. Date: Jan. 20, 2022

(65) Prior Publication Data
US 2023/0277434 A1 Sep. 7, 2023

(30) Foreign Application Priority Data
Jul. 17, 2020 (FR) ...................................... 2007524

(51) Int. Cl.
*A61K 8/89* (2006.01)
*A61Q 1/06* (2006.01)

(52) U.S. Cl.
CPC .................. *A61K 8/89* (2013.01); *A61Q 1/06* (2013.01); *A61K 2800/31* (2013.01); *A61K 2800/43* (2013.01)

(58) Field of Classification Search
None
See application file for complete search history.

(56) References Cited

U.S. PATENT DOCUMENTS

2003/0099604 A1* 5/2003 Light ....................... A61Q 1/06
424/74
2005/0265943 A1* 12/2005 Geffroy-Hyland .... A61K 8/895
424/70.12

2007/0128233 A1* 6/2007 Lu ........................ A61K 8/0283
424/401
2009/0068238 A1 3/2009 Themens et al.
2009/0092567 A1 4/2009 Chou et al.
2021/0330574 A1 10/2021 Saito et al.

FOREIGN PATENT DOCUMENTS

| | | |
|---|---|---|
| FR | 2922104 A1 | 4/2009 |
| FR | 2924936 A1 | 6/2009 |
| FR | 2968983 A1 | 6/2012 |
| JP | 2008-88099 A | 4/2008 |
| JP | 2019-14670 A | 1/2019 |
| WO | WO-2009/042832 A2 | 4/2009 |
| WO | WO 2019/002311 * | 1/2019 |
| WO | WO-2019/002311 A1 | 1/2019 |
| WO | WO-2019/180387 A1 | 9/2019 |
| WO | WO 2020/075792 A1 | 4/2020 |

OTHER PUBLICATIONS

Hansen, The Three dimensional solubility parameters, J Paint Technol., 39: 105 (1967).
International Search Report for International Patent Application No. PCT/FR2021/051333, dated Oct. 20, 2021.
Techincal Data Sheet DOWSIL(TM) EL-9241 DM Silicone Elastomer Blend, 1-3 (Jan. 2017).
Chinese Office Action for Chinese Application No. 202180050324.4, dated Nov. 22, 2024, with English translation.
Japanese Office Action for Japanese Application No. 2023-502974, dated Aug. 12, 2025, with English translation.
Chinese Office Action for Chinese Application No. 202180050324.4, dated Jun. 25, 2025, with English translation.

* cited by examiner

*Primary Examiner* — Danah Al-Awadi
(74) *Attorney, Agent, or Firm* — Birch, Stewart, Kolasch & Birch, LLP

(57) ABSTRACT

A cosmetic composition that is preferably anhydrous and includes, in a physiologically acceptable medium, at least: one or more organopolysiloxane elastomer(s), preferably at least one organopolysiloxane elastomer carried in a first oil, an apolar oil that differs from the first oil, a polar wax, the total content of the organopolysiloxane elastomer active material(s) being greater than or equal to 7%, preferably greater than or equal to 10% by weight relative to the total weight of said composition.

9 Claims, No Drawings

COSMETIC COMPOSITION FOR THE LIPS

CROSS REFERENCE TO RELATED APPLICATIONS

This application is a U.S. National Stage of International Patent Application No. PCT/FR2021/051333 filed on Jul. 16, 2021, which claims the benefit of priority of French Patent Application No. 2007524 filed Jul. 17, 2020, the respective disclosures of which are each incorporated herein by reference in their entireties.

FIELD OF THE INVENTION

The present invention relates to a care and/or make-up composition for the lips.

PRIOR ART

Lip care and make-up products intended to embellish, protect and/or colour the lips are widespread. In particular, products for the lips are known in liquid, semi-fluid or solid (stick) form for a glossy deposit or matt deposit on the lips and having, for make-up products, good colour retention properties. In order to provide mattness, volatile oils and fillers are generally used, but the stability of the composition can be affected and the deposit of the film can have a desiccating appearance on the lips.

There is therefore still a need to develop novel lip care and/or make-up products, in particular solid products in order to obtain a homogeneous, comfortable and matt deposit that is not desiccating on the lips. Consumers also desire soft properties on application, with a "velvety" effect.

The present invention responds to these needs. Indeed, the applicant has developed a composition comprising a total content of organopolysiloxane elastomers active ingredient greater than or equal to 7%, preferably greater than or equal to 10%, by weight of the total composition, in an oily phase containing at least one non-polar oil and a polar wax. Unexpectedly, the inventors have obtained a composition having very good stability despite the incompatibility of the silicone compounds (organopolysiloxane elastomers) at a high content with the non-silicone compounds of the oily phase, and on the other hand the incompatibility of the non-polar oil with the polar wax, with the desired properties of mattness, comfort and hydration on application, with a velvety deposit.

DISCLOSURE OF THE INVENTION

The invention relates, according to a first aspect, to a cosmetic composition comprising, in a physiologically acceptable medium, at least:
  one or more organopolysiloxane elastomers, preferably an organopolysiloxane elastomer conveyed in a first oil,
  a non-polar oil, distinct from the first oil,
  a polar wax,
the total content of organopolysiloxane elastomer active ingredient being greater than or equal to 7%, preferably greater than or equal to 10% by weight relative to the total weight of said composition.

The invention also relates to a method for cosmetic care and/or make-up of the lips, comprising the application, on the lips, of at least one layer of a composition according to the invention.

DETAILED DESCRIPTION OF THE INVENTION

A first object of the invention is thus a cosmetic composition comprising, in a physiologically acceptable medium, at least:
  one or more organopolysiloxane elastomers, preferably an organopolysiloxane elastomer conveyed in a first oil,
  a non-polar oil, distinct from the first oil,
  a polar wax,
the total content of organopolysiloxane elastomer active ingredient being greater than or equal to 7%, preferably greater than or equal to 10% by weight, relative to the total weight of said composition.

According to a particular and preferred embodiment, the composition of the invention is an anhydrous composition.

The term "anhydrous" shall mean, in particular, that water is preferably not deliberately added to the compositions but may be present in trace amounts in the various compounds used in the compositions. In particular, the composition according to the invention comprises less than 4% by weight water, preferably less than 3%, preferably less than 2%, more preferably less than 1%, yet more preferably less than 0.5% by weight water, relative to the total weight of said composition, or is even totally devoid of water.

The composition of the invention is generally a solid composition.

The term "solid" shall mean a composition having, at a temperature of 20° C. and atmospheric pressure (760 mm Hg), a hardness greater than 30 Nm$^{-1}$, preferably greater than 40 Nm$^{-1}$.

The hardness can be measured at 20° C. by the so-called "butter wire" method, which consists of transversely cutting a baton of preferably cylindrically symmetric product, using a rigid metal wire of diameter 250 μm by moving the wire relative to the stick at a speed of 60 mm/min. The hardness of the samples is expressed in grams-force (gf) and can be measured by means of a texture analyser such as a TAXT Plus Texture Analyser. Preferably, the value obtained will be between 140 and 190.

The cosmetic composition of the invention comprises a fatty or oily phase.

The term "oily phase" shall mean an oil or a mixture of mutually miscible oils.

Within the meaning of the invention, the term "oil" shall mean a fatty body that is not soluble in water and is liquid at 25° C. and atmospheric pressure.

The composition of the invention comprises at least one first oil, which serves to convey the organopolysiloxane elastomer and a second oil distinct from the first oil. These oils are described below.

Organopolysiloxane Elastomer

The composition of the invention comprises one or more organopolysiloxane elastomers at a total content of organopolysiloxane elastomer active ingredient of at least 7%, preferably at least 10% by weight relative to the total weight of said composition.

In particular, the total content of organopolysiloxane elastomer active ingredient will be greater than 10% to 30%, in particular from 10% to 20% by weight, relative to the total weight of said composition.

The organopolysiloxane elastomer can be chosen from the group consisting of organopolysiloxane elastomers conveyed in an oil, organopolysiloxane elastomer powders, optionally coated with silicone resin, and the mixtures thereof.

According to a particular embodiment of the invention, the composition comprises at least one organopolysiloxane elastomer conveyed in an oil as described below.

According to a particular and preferred embodiment, the composition of the invention comprises at least one organopolysiloxane elastomer conveyed in an oil and an organopolysiloxane elastomer powder distinct from the above-described organopolysiloxane elastomer conveyed in an oil, said organopolysiloxane elastomer powder being coated or not coated with silicone resin.

The combination of these particular elastomers makes it possible to obtain a deposit that is matt and comfortable (flexibility of the deposit, absence of desiccating sensation), as well as a velvety and soft sensation.

These compounds and their respective contents are described below.

Organopolysiloxane Elastomer Conveyed in a First Oil

Within the meaning of the invention, the term "conveyed" shall mean that the elastomer is transported in the composition in a pre-dispersed form in at least a first oil, in particular in the form of a homogeneous mixture of elastomer particles dispersed in the first oil, that is stable for at least 24 hours at 20° C. Preferably, this elastomer is in the form of a gel in at least a first oil.

The term "organopolysiloxane elastomer" or "silicone elastomer" shall mean a flexible, deformable organopolysiloxane having viscoelastic properties and, in particular, the consistency of a sponge or a flexible sphere. Its modulus of elasticity is such that this material resists deformation and has a limited capacity for extension and contraction. This material is capable of returning to its original shape following stretching.

More particularly, it is a cross-linked silicone elastomer.

The elastomer can be chosen among non-emulsifying or emulsifying elastomers. Preferably, it is a non-emulsifying elastomer.

The term "non-emulsifying" defines organopolysiloxane elastomers which do not contain a hydrophilic chain, and in particular not containing polyoxyalkylene units (in particular polyoxyethylene or polyoxypropylene units), nor polyglyceryl units.

Hence, the organopolysiloxane elastomer can be obtained by:

a cross-linking addition reaction of diorganopolysiloxane containing at least one hydrogen bonded to silicon and diorganopolysiloxane having ethylenically unsaturated groups bonded to silicon, in particular in the presence of a platinum catalyst;

or by a cross-linking, hydrogenation, condensation reaction between a diorganopolysiloxane with hydroxyl end groups and a diorganopolysiloxane containing at least one hydrogen bonded to silicon, in particular in the presence of an organotin;

or a cross-linking condensation reaction of a diorganopolysiloxane with hydroxyl end groups and a hydrolysable organopolysiloxane;

or by thermal cross-linking of organopolysiloxane in particular in the presence of an organic peroxide catalyst;

or by cross-linking organopolysiloxane by high-energy radiation such as gamma rays, ultra-violet rays or an electron beam.

Preferably, the organopolysiloxane elastomer is obtained by a cross-linking addition reaction (A) of diorganopolysiloxane containing at least two hydrogens, each bonded to a silicon, and (B) diorganopolysiloxane having at least two ethylenically unsaturated groups bonded to silicon, in particular in the presence (C) of a platinum catalyst.

In particular, the organopolysiloxane elastomer can be obtained by reaction of dimethylpolysiloxane with dimethylvinylsiloxy end groups and methylhydrogen polysiloxane with trimethylsiloxy end groups, in the presence of a platinum catalyst.

Compound (A) is the base reagent for forming organopolysiloxane elastomer and the cross-linking takes place by addition reaction of compound (A) with compound (B) in the presence of the catalyst (C).

Compound (A) is, in particular, an organopolysiloxane having at least two hydrogen atoms bonded to distinct silicon atoms in each molecule.

Compound (A) may have any molecular structure, in particular a linear chain or branched chain structure or a ring structure.

Compound (A) can have a viscosity at 25° C. ranging from 1 to 50,000 centistokes, in particular in order to be easily miscible with compound (B). The organic groups bonded to the silicon atoms of compound (A) may be alkyl groups such as methyl, ethyl, propyl, butyl, octyl; substituted alkyl groups such as 2-phenylethyl, 2-phenylpropyl, 3,3,3-trifluoropropyl; aryl groups such as phenyl, tolyl, xylyl; substituted aryl groups such as phenylethyl; and substituted monovalent hydrocarbon groups such as an epoxy group, a carboxylic ester group or a mercapto group.

Compound (A) can both be chosen from methylhydrogenpolysiloxanes with trimethylsiloxy end groups, dimethylsiloxane-methylhydrogensiloxane copolymers with trimethylsiloxy end groups, and cyclic dimethylsiloxane-methylhydrogensiloxane copolymers.

Compound (B) is advantageously a diorganopolysiloxane having at least two lower alkenyl groups (for example C2-C4); the lower alkenyl group may be chosen from vinyl, allyl and propenyl groups. These lower alkenyl groups can be located in any position on the organopolysiloxane molecule but preferably not located at the ends of the organopolysiloxane molecule. Organopolysiloxane (B) can have a branched chain, linear chain, ring or network structure but the linear chain structure is preferred. Compound (B) can have a viscosity ranging from the liquid state to the rubber state. Preferably, compound (B) has a viscosity of at least 10° centistokes at 25° C.

In addition to the above mentions alkenyl groups, the other organic groups bonded to the silicon atoms in compound (B) can be alkyl groups such as methyl, ethyl, propyl, butyl or octyl; substituted alkyl groups such as 2-phenylethyl, 2-phenylpropyl or 3,3,3-trifluoropropyl; aryl groups such as phenyl, tolyl or xylyl; substituted aryl groups such as phenylethyl; and substituted monovalent hydrocarbon groups such as an epoxy group, a carboxylic ester group, or a mercapto group.

The organopolysiloxanes (B) can be chosen from methylvinylpolysiloxanes, methylvinylsiloxane-dimethylsiloxane copolymers, dimethylpolysiloxanes with dimethylvinylsiloxy end groups, dimethylsiloxane-methylphenylsiloxane copolymers with dimethylvinylsiloxy end groups, dimethylsiloxane-diphenylsiloxanemetliylvinylsiloxane copolymers with dimethylvinylsiloxy end groups, dimethylsiloxanemethylvinylsiloxane copolymers with trirnethylsiloxy end groups, dimethylsiloxanemethylphenylsiloxane-methylvinylsiloxane copolymers with trirnethylsiloxy end groups, methyl (3,3,3-trifluoropropyl) polysiloxane with dimethylvinylsiloxy end groups, and dimethylsiloxane-methyl (3,3,3-trifluoropropyl) siloxane copolymers with dimethylvinylsiloxy end groups.

In particular, the organopolysiloxane elastomer can be obtained by reaction of dimethylpropylisoxane with dimethylvinylsiloxy end groups and methylhydrogenpolysiloxane with trimethylslioxy end groups, in the presence of a platinum catalyst. According to another alternative, compound (B) can be an unsaturated hydrocarbon compound having at least two lower alkenyl groups (for example with C2-C4); the lower alkenyl group can be chosen from the vinyl, allyl and propenyl groups. These lower alkenyl groups can be located in any position on the molecule but are preferably located at the ends. Examples include hexadiene, and in particular the 1,5-hexadiene.

Advantageously, the sum of the number of ethylenic groups per molecule of compound (B) and the number of hydrogen atoms bonded to silicon atoms per molecule of compound (A) is at least 5.

It is advantageous that compound (A) is added in a quantity such that the molecular ratio between the total quantity of hydrogen atoms bonded to silicon atoms in compound (A) and the total quantity of all the ethylenically unsaturated groups in compound (B) is in the range from 1,5/1 to 20/1.

Compound (C) is the cross-linking reaction catalyst and is, in particular, chloroplatinic acid, chloroplatinic acid-olefin complexes, chloroplatinic acid-alkenylsiloxane complexes, chloroplatinic acid-diketone complexes, platinum black and the platinum on the support. The catalyst (C) is preferably added at from 0.1 to 1000 parts by weight, better from 1 to 100 parts by weight, as clean platinum metal for 1000 parts by weight of the total quantity of compounds (A) and (B).

Examples of non-emulsifying elastomers which can be used include those sold under the names DOWSIL Silicone Elastomer Blend such as that conveyed in a non-volatile oil sold under the name "DOWSIL, 9041" and "DOWSIL, EL-9241 DM" by Dow Chemical Company, as well as those conveyed in a volatile oil sold under the name "DOWSIL EL-8040 ID", "DOWSIL EL-9140 DM", "DOWSIL EL-9240 DM", "DOWSIL EL-9048", "DOWSIL 9040", "DOWSIL 9045", "DOWSIL EB-9586", "DOWSIL 9546" by the Dow Chemical Company.

Mention can also be made to those sold under the names "KSG-15". "KSG-1510", "USG-1G3", "USG-106", "KSG-16", "KSG-1610", "KSG-18A", "KSG-19", "KSG-016F", KSG-41 A", "K SG-42 A", "KSG-43", "KSG-44" "KSG-042Z" "SG-045Z", "KSG Q48Z" by Shin Etsu. Other non-emulsifying elastomers conveyed in a non-volatile or weakly volatile oil are also sold under the names "Gransil DM-10", "Gransil DMAM", "Gransil DMG-20", "Gransil DMG-6", "Gransil PM" by Grant Industries; or those conveyed in a mixture of oils sold under the names "Gransil OHS-5", "Gransil PS-5" by Grant industries; or those conveyed in a volatile oil sold under the names "GI CD-10", "GI CD-11". "Gransil DMG-" Gransil DMG-3". "Gransil GCM-5", "Gransil GTS", "Gransil G VL", "Gransil GVL-HV", "Gransil IDS-5", "Gransil MLB", "Gransil PC-12", "Gransil PC-12P", "Gransil RPS", "Gransil RPS-D6", "GI CD-965", "Gransil DM-5", "Gransil DMCM-5", "Gransil DMDM-25", "Gransil DMDM-35", "Gransil DMID", "Gransil DMT3" "Gransil G AM" by Grant Industries.

The content of organopolysiloxane elastomer(s) active ingredient conveyed in a first oil, for the most concentrated commercial references (high dry matter content) can range from 10% to 30% by weight, in particular from 10% to 20% by weight relative to the total weight of the composition.

According to a particular embodiment, in particular when the composition comprises the combination of an organopolysiloxane elastomer conveyed in an oil and an organopolysiloxane elastomer powder distinct from the above described elastomer, the composition according to the invention comprises a content of organopolysiloxane elastomer(s) conveyed in a first oil, with a dry matter content (active ingredient) ranging from 0.1% to 10%, in particular 1% to 8%, preferably from 2% to 6% by weight, relative to the total weight of the composition. The term "first oil" shall mean the oil in which the organopolysiloxane elastomer is conveyed. This first oil is chosen from non-volatile oils and volatile oils, preferably non-volatile oils. It is, in particular, a silicone oil.

In the context of the invention, "silicone oil" shall mean an oil comprising at least one silicon atom, and in particular an $Si$—$O$ group.

Examples include non-volatile polydimethylsiloxanes (PDMS), polydimethylsiloxanes including at least one $C_{2-24}$, alkyl or alkoxy group that is hanging and/or at the end of the silicone chain. Polydimethylsiloxanes include, in particular, heptamethyl hexyltrisiloxane, heptamethyloctyl trisiloxane, hexamethyl disiloxane, octamethyl trisiloxane, decamethyl tetrasiloxane, dodecamethyl pentasiloxane and the mixtures thereof. In particular, the first oil is chosen from linear polydimethylsiloxanes of viscosity between 5 cSt and 100 cSt (centistokes); or one of the mixtures thereof.

According to a particular embodiment, the composition of the invention further comprises an organopolysiloxane elastomer powder, distinct from the above-described organopolysiloxane elastomer conveyed in the first oil.

Organopolysiloxane Elastomer Powder, Coated or not with Silicone Resin

Hence, according to a particular embodiment, the composition of the invention further comprises an organopolysiloxane elastomer powder distinct from the organopolysiloxane elastomer described above conveyed in the first oil, said organopolysiloxane elastomer powder being coated or not coated with silicone resin. Advantageously, the composition further comprises at least one organopolysiloxane elastomer powder coated with silicone resin.

According to a particular embodiment, the composition according to the invention comprises an organopolysiloxane elastomer powder that is not coated with silicone resin. It is possible to use as elastomers in the form of a powder, those sold under the names "DC9505", "DC 9506" by Dow Corning and with name INCI Dimethicone/Vinyl Dimethicone Crosspolymer.

According to another particular and preferred embodiment, the composition according to the invention comprises an organopolysiloxane elastomer powder coated with silicone resin, in particular silsesquioxane resin, as described for example in patent U.S. Pat. No. 5,538,793. Such elastomer powders are sold under the names "KSP-100", "KSP-101", "KSP-102", "KSP-103", "KSP-104", "KSP-105" by Shin Etsu, and have INCI name "vinyl dimethicone/methicone silsesquioxane crosspolymer".

Preferably, the organopolysiloxane elastomer powder coated with silicone resin is a compound with INCI name "vinyl dimethicone/methicone silsesquioxane crosspolymer". Preferably, the composition according to the invention comprises an organopolysiloxane elastomer powder coated with silicone resin, in particular silsesquioxane resin, at a content ranging from 1% to 20% by weight, in particular from 5% to 15%, preferably from 7% to 11% by weight, relative to the total weight of the composition.

According to a particular and preferred embodiment, the composition also comprises an organopolysiloxane elastomer conveyed in a non-volatile oil combined with at least one organopolysiloxane elastomer powder, advantageously coated with a silicone resin.

Hence, according to a particular embodiment, the content of organopolysiloxane elastomer active ingredient conveyed in an oil ranges from 0.1% to 10%, in particular 1% to 8%, preferably from 2% to 6% by weight relative to the total weight of the composition and the content of organopolysiloxane elastomer powder ranges from 1% to 20%, in particular 5% to 15%, preferably 7% to 11% by weight relative to the total weight of the composition.

Non-Polar Oil

The cosmetic composition according to the invention comprises at least one "second oil", distinct from the first oil mentioned above. This second oil is chosen from non-volatile oils or volatile oils, or the mixture thereof, preferably non-volatile oils.

The second oil according to the invention is a "non-polar oil" otherwise referred to as an "apolar oil".

Within the meaning of the invention, "non-polar oil" shall mean an oil for which the solubility parameter at 25° C., da, is equal to 0 $(J/cm^3)^{1/2}$. The definition and calculation of the HANSEN three-dimensional solubility parameters are described in the article by C. M. HANSEN: "The three dimensional solubility parameters" J. Paint Technol. 39, 105 (1967).

The non-polar oil may be a silicon oil or a hydrocarbon oil.

In particular, it will be a non-polar hydrocarbon oil.

The non-polar hydrocarbon oil can be chosen from linear or branched hydrocarbons of mineral or synthetic origin, such as: paraffin oil or the derivatives thereof, squalane, iso-icosane, naphthalene oil, polybutylenes, hydrogenated polyisobutylenes, decene/butene copolymers, polybutene/polyisobutene copolymers, polydecenes and hydrogenated polydecenes, and the mixtures thereof.

Preferably, the composition of the invention comprises at least one non-polar oil chosen from polybutylenes, hydrogenated polyisobutylenes, decene/butene copolymers, polybutene/polyisobutene copolymers, hydrogenated polydecenes and polydecenes, more preferably hydrogenated polydecenes.

The content of non-polar oil(s) according to the invention would generally range from 15% to 45%, in particular from 20% to 40%, by weight relative to the total weight of said composition.

The composition of the invention may further comprise other additional oils chosen from hydrocarbon oils, silicone oils and the mixtures thereof.

According to a particular embodiment, the composition further comprises at least one polar hydrocarbon oil.

Within the meaning of the invention, the term "polar oil" shall mean an oil for which the solubility parameter at 25° C., da, is not equal to 0 $(J/cm^3)^{1/2}$.

In particular, the polar hydrocarbon oil or oils comprise at least one alcohol fraction (it is then an "alcohol oil") or at least one ester function (it is then an "ester oil").

The "alcohol oils" include, in particular, C10-C26, more particularly C10-C24, and preferably C12-C22, saturated or unsaturated, branched or unbranched alcohols, more particularly monoalcohols. More particularly, the C10-C26 alcohols are fatty monoalcohols that are preferably branched when they comprise at least 16 carbon atoms. By way of example, fatty alcohols that can be used according to the invention include linear or branched fatty alcohols, of synthetic or natural origin. Particular examples of fatty alcohols that can be preferably used include, in particular, lauric, isostearylic and oleic alcohols, 2-butyloctanol, 2-undecyl pentadecanol, 2-hexyldecylic alcohol, isocetylic alcohol, octyldodecanol and the mixtures thereof. According to an advantageous embodiment of the invention, the fatty alcohol is octyldodecanol.

Thus, according to a particular embodiment, the composition of the invention also comprises octyldodecanol.

According to a particular embodiment, the composition of the invention further comprises a polar oil.

The "ester oils" include, in particular:

fatty acid esters, in particular with 4 to 22 carbon atoms, synthetic esters such as oils of formula $R_1COOR_2$ in which $R_1$ represents the residue of a linear or branched fatty acid having 4 to 40 carbon atoms and $R_2$ represents an, in particular branched, hydrocarbon chain containing 4 to 40 carbon atoms provided that $R_1+R_2$ is ≥16, such as, for example, isononyl isononanoate, 2-hexyl palmitate, octyldodecyl neopentanoate, octyl-2 dodecyl stearate, isostearyl isostearate, octyl-2 dodecyl benzoate, isopropyl myristate, isopropyl palmitate, butyl stearate, hexyl laurate, 2-ethyl-hexyl palmitate, 2-hexyl-decyl laurate, 2-octyl-decyl palmitate, 2-octyl-dodecyl myristate, and 2-diethyl-hexyl succinate;

linear fatty acid esters having a total carbon number ranging from 35 to 70;

hydroxyl esters, preferably having a total carbon number ranging from 35 to 70, such as polyglycerol-2 triisostearate, isostearyl lactate, octyldodecyl hydoxystearate, diisostearyle malate, glycerine stearate; diethylenegly-col diisononanoate;

aromatic acid esters and alcohols comprising 4 to 22 atoms fatty alcohol esters or branched C24-C28 fatty acids polyesters resulting from the esterification of at least one carboxylic acid triglyceride, hydroxylated by an aliphatic monocarboxylic acid, that is optionally unsaturated, and the mixtures thereof.

A composition according to the invention can thus comprise, according to a particular embodiment, a content of polar oil(s) ranging from 1% to 15%, for example from 2% to 10% by weight relative to the total weight of the composition.

The total quantity of oils present in the composition according to the invention is between 40% and 75% by weight, preferably between 50% and 70%, relative to the total weight of the composition.

Polar Wax

The composition according to the invention comprises at least one polar wax.

Within the meaning of the present invention, the term "wax" shall mean a solid compound at 25° C. which undergoes a reversible solid/liquid change of state and has a melting temperature greater than 30° C., preferably greater than 45° C.

In particular, the polar wax is chosen from the group comprising beeswax, camauba wax, candelilla wax, cotton wax, rice bran wax, sunflower wax, bay wax, Chinese insect wax, montan wax, lanolin and the acetylated, esterified, polyethoxylated alcohol derivatives thereof, kapok wax, sugar cane wax, hexyl laurate, jojoba wax, shellac wax, polyethoxylated cholesterol ether, synthetic beeswaxes marketed by Koster Keunen under the tradename Kester Wax K82H, or one of the mixtures thereof.

According to a particular embodiment, the composition of the invention comprises one or more polar waxes chosen from the group consisting of candelilla wax, beeswax, carnauba wax, rice bran wax, sunflower wax, jojoba wax and the mixtures thereof, preferably candelilla wax.

According to a preferred embodiment, the composition of the invention comprises at least one candelilla wax as polar wax.

The polar wax content in the composition of the invention will generally be from 0.5% to 10%, preferably from 1% to 5% by weight relative to the total weight of said composition.

The composition may further comprise a non-polar wax.

The term "non-polar wax" shall mean a hydrocarbon wax and/or a silicone wax. The term "non-polar hydrocarbon wax" shall mean a wax comprising only carbon and hydrogen atoms and not comprising heteroatoms such as oxygen, nitrogen, silicon or phosphorus. In particular, it is possible to use, as a non-polar wax, monocrystalline waxes, paraffins, ozokerite, polyethylene waxes and the mixtures thereof, preferably polyethylene waxes.

The term "non-polar silicone wax" shall mean a wax comprising a heteroatom of silicon.

Examples of non-polar silicone waxes include C20-24 alkyl dimethicone, marketed by Siltech under the name Silwax D2024; C24-28 alkyl dimethicone, marketed by Evonik Industries AG under the name Abil Wax, or one of the mixtures thereof.

The non-polar wax content in the composition of the invention can range from 0.5 to 12%, in particular from 2% to 10%, or even from 4% to 8% by weight relative to the total weight of said composition.

According to a particular embodiment, the composition of the invention will further comprise the polar wax, also a non-polar wax, preferably chosen from polyethylene waxes.

Hence, according to a particular embodiment, the composition of the invention comprises at least one candelilla wax and a polyethylene wax.

In particular, a composition according to the invention may comprise a total waxes content ranging from 5% to 20%, for example from 6% to 15% by weight, preferably from 7% to 12% by weight, relative to the total weight of the composition.

According to a particular embodiment, the total wax(es) content in the composition of the invention is greater than or equal to 5% by weight relative to the total weight of said composition.

Additional Ingredients

The composition of the invention may further comprise a fatty pasty substance.

Fatty Pasty Substance

The term "fatty pasty compound" or "pasty compound" or "fatty pasty substance" shall mean a non-crystalline fatty compound comprising, at a temperature of 25° C., a liquid fraction and a solid fraction.

The pasty compound is, for example, chosen from the group consisting of lanolin and its derivatives, silicone polymer compounds, alkyl methacrylate copolymers, preferably having a C8-C30 alkyl group, homo-oligomers and copolymers of vinyl esters having C8-C30 alkyl groups, homo-oligomers and copolymers of vinyl-ethers having C8-C30 alkyl groups, liposoluble polyethers resulting from the polyetherification between one or more C2-C50 diols, ethylene-oxide and/or propylene-oxide copolymers with C6-C30 long-chain alkylene oxides, diglycerol esters, arachidyl propionate, phytosterol esters, non-cross-linked polyesters resulting from the polycondensation between a C4-C50 branched or linear carboxylic diacid or a polyacid and a diol or a polyol, the ester resulting from the esterification reaction of hydrogenated castor oil with isostearic acid such as a mono-di- or tri-isostearate of hydrogenated castor oil, a mixture of soya sterols and pentaerythritol oxyethylene (5 OE) oxypropylene (5 OP), fatty acid triglycerides and their derivatives, shea butter, cocoa butter, mango oil or butter, and the mixtures thereof.

Fillers

The composition may further comprise at least one additional filler that is distinct from the silicone elastomer powder.

Within the meaning of the invention, the term "fillers" shall mean particles of any shape, colourless or white, mineral or organic, natural or synthetic, which are insoluble and dispersed in the medium of the composition. These fillers serve in particular to modify the rheology or the texture of the composition and/or provide a matt effect. The fillers can be mineral or organic and of any shape: platelets, spherical or oblong.

The "fillers" are chosen, in particular, from silicas, micas, of natural or synthetic origin, kaolin, zinc and titanium oxides; calcium carbonate, magnesium carbonate and bicarbonate; zinc, magnesium or lithium stearate, zinc laurate, magnesium myristate; synthetic polymer powders such as polyethylene, polyesters, polyamides (for example nylon); polyacrylic or polymethacrylic acid powders, mineral powders such as spherical silica; spherical titanium dioxides; glass and ceramic beads; organic material powders of natural origin such as starches from corn, wheat and rice, cross-linked or not, and the mixtures thereof.

According to a particular embodiment, silica, cellulose powder and the mixture thereof are used.

A composition according to the invention may have a content of filler(s) ranging from 0.5% to 10%, for example from 1% to 8% by weight, preferably from 2% to 7% by weight, relative to the total weight of the composition.

Colouring Materials

A composition conforming to the present advantageously comprises, for make-up of the lips, at least one "colouring material" which can be chosen from water-soluble or insoluble, liposoluble or not, organic or inorganic colouring materials, materials with optical effects and the mixtures thereof.

Within the meaning of the present invention, the term "colouring material" shall mean a compound that is able to produce a coloured optical effect when it is formulated in sufficient quantity in an appropriate cosmetic medium According to a particular embodiment, the colouring material or materials are chosen, in particular, among mineral and/or organic pigments, composite pigments (based on mineral and/or organic materials), colouring agents, mother-of-pearl or pearlescent pigments, and the mixtures thereof.

The term 'colouring agents' shall mean colouring agents that are conventionally used in the field of cosmetics, distinct from food colouring agents used in food products.

According to a particular embodiment, the composition of the invention comprises at least one colouring material chosen from mineral and/or organic pigments, composite pigments (based on mineral and/or organic materials), mother-of-pearl or pearlescent pigments, and the mixtures thereof.

Mineral and Organic Pigments

"Pigments" shall mean mineral or organic, white or coloured particles, insoluble in an aqueous solution, intended for colouring and/or opacifying the resulting deposit. These can include mineral pigments, organic pigments and composite pigments (in other words pigments based on mineral and/or organic materials).

The "mineral pigments" include, for example, titanium dioxide; black, yellow, red and brown iron oxides and manganese violet.

The "organic pigments" can include, for example, pigments D & C red no. 19; D & C red no. 9; D & C Red no. 22; D & C Red no. 21; D & C Red no. 28; D & C Yellow no. 6; D & C orange no. 4; D & C orange no. 5; D & C Red no. 27; D & C red no. 13; D & C Red no. 7; D & C Red no. 6; D & C Yellow no. 5; D & C Red no. 36; D & C Red no. 33; D & C orange no. 10; D & C yellow no. 6; D & C Red no. 30; D &C red no. 3; D &C Blue 1; carbon black and cochineal carmine based lacquers.

Colouring Agents

The "colouring agents" may include Yellow 5, Yellow 6, Blue 1, Green 5, Green 3, Green 6, Orange 4, Red 4, Red 21, Red 22, Red 27, Red 28, Red 33, Red 40, cochineal carmine (CI 15850, CI 75470). Liposoluble colouring agents are, for example, Sudan red, D&C Red 17, D&C Green 6, beta-carotene, Sudan brown, D&C Yellow 11, D&C Violet 2, D&C orange 5, quinoline yellow and annatto.

In particular, the total content of colouring materials in the composition can range from 1% to 15% by weight, in particular from 2% to 10% by weight, more preferably from 3% to 8% by weight relative to the total weight of the composition.

Galenic

The composition of the invention is a care and/or make-up composition of keratin materials, in particular a lip care and/or make-up composition.

The composition of the invention is generally a solid composition such as previously defined.

Make-up compositions for the lips can include, in particular, a lipstick, a lip contour pencil or a lip balm.

According to a particular and preferred embodiment, it is a solid lip make-up composition, in particular a stick or lipstick.

Cosmetic Method

The invention also relates to a method for cosmetic care and/or make-up of the lips, comprising the application of a composition according to the invention.

The composition applied on the lips is preferably a solid lip make-up composition, in particular a stick or lipstick.

The method according to the invention is, in particular, a method for make-up of the lips, intended to deposit on said lips a comfortable, matt, non-desiccating film, with good colour hold.

The invention will be illustrated by means of the following non-limiting examples. The percentages are expressed in percentage by weight relative to the total weight of the composition, unless otherwise indicated.

EXAMPLES

Example 1: Effect of the Presence of a Polar Wax in the Composition of the Invention Two comparative formulas were tested, one with the presence of a polar wax (invention) and the other without the presence of polar wax (comparative). The polar wax used was candelilla wax.

The implementation of the said compositions was evaluated, as well as the stability and sensory properties of the composition.

The results are presented in the following table:

TABLE 1

| Ingredients | Composition outside of the invention (without polar wax) | Composition according to the invention (with polar wax) |
|---|---|---|
| Silicone elastomer conveyed in an oil (DOWSIL EL 9241 DM) | 25 | 25 |
| Silicone oil (DIMETHICONE 100 CS) | 7.8 | 7.8 |
| Lecithin EMULMETIK 300 IP | 0.5 | 0.5 |
| UNIPURE RED LC | 0.9875 | 0.9875 |
| C 339001 SUN PURO | 2.48 | 2.48 |
| UNIPURE RED LC | 0.77 | 0.77 |
| SUNCROMA FDC YELLOW 6 AL LAKE | 4.8 | 4.8 |
| SUNCROMA FDC YELLOW 5 AL LAKE | 2.6 | 2.6 |
| UNIPURE RED LC | 5.55 | 5.55 |
| Hydrogenated polydecene DEKANEX 2006 FG (non-polar oil) | 28.0325 | 28.0325 |
| Polyethylene wax PERFORMALENE 500 (non-polar wax) | 7.45 | 5.2 |
| Candelilla wax CANDELILLA WAX SR 3 (polar wax) | — | 2.5 |
| Silica SUNSPHERE H33 | 3 | 3 |
| Silica SILICA SHELLS | 2 | 2 |
| Silicone elastomer powder coated with silicone resin (KSP-100) | 3 | 3 |
| Calcium carbonate | 0.05 | 0.05 |
| Shea butter | 1.5 | 1.5 |
| Stability | Presence of holes in the sticks, impossible to have a complete stick | OK |
| Sensory properties | Difficult to cast a correct stick | OK |

The compositions are prepared according to the following protocol:

the silicone elastomer conveyed in an oil (Dowsil 9241 EL) and Dimethicone 100cs are mixed under stirring at 95° C.; when the mixture is homogeneous, the polyethylene and candelilla waxes are incorporated;

the pigmentary paste comprising the pigments, hydrogenated polydecene and lecithin is added to the mixture prepared above when the waxes are melted, then the powders are sprinkled (fillers: silica shells, sunsphere H33 and KSP 100) under stirring;

the mixture at a temperature greater than 95° C. is poured into a mould.

The lipsticks are evaluated for several criteria:

Organoleptic properties: sensory properties, colour: the compositions undergo sensory testing for their properties of comfort, mattness and coverage.

Physicochemical properties: hardness, breakage test: the physicochemical measurements ensure the possible shaping of the composition of the invention, the strength of the stick during application and its breakage. In practice, the sticks are placed at 20° C. for 24 h. They are then cut at 1 cm from the cup using a wire in order to measure the hardness of the stick. The operation is carried out three times in order to produce an average. The hardness makes it possible to predict the behaviour of the stick on release from the mould, on breaking and during application. A texture analyser is used for the hardness measurement, the TAXT Plus and the Exponent software. The value obtained, expressed in grams force (Gf), must be between 140 and 190.

Stability: The formulas are monitored in various ovens in order to reproduce the life of the product. These accelerated ageing tests make it possible to ensure that the product is stable over time. The durability of the product can also be confirmed under normal conditions of storage and use. In practice, the stability of the sticks is observed after passage through various ovens: humidity, alternation between 4° C. and 45° C. The parts are stabilised 24 hours after their manufacture. The samples are observed after a defined time in each oven, 24 hours, 2 weeks, 1 month, 3 months. The absence of colour drift is observed, as well as the absence of drops, exudation and changes in the appearance of the stick: glossiness, mattness.

The results show that the presence of the polar wax in the composition of the invention makes it possible to obtain a stable composition which has the desired organoleptic and physicochemical properties, compared with the same composition without polar wax.

This composition makes it possible to obtain a matt stick with high coverage, having a rather "rigid" structure in order to have an unguided and comfortable structure (no tightness over time). The term 'unguided structure' shall mean a formulation for application with the stick (lipstick tube) present outside of the mechanism

Example 2: Effect of the Presence of a Polar Wax in a Composition of the Invention Two formulas are compared, one with the presence of a polar wax (invention) and the other without the presence of polar wax (comparative). The polar wax used is candelilla wax.

TABLE 2

| Ingredients | Composition outside of the invention (without polar wax) | Composition according to the invention (with polar wax) |
| --- | --- | --- |
| Silicone elastomer conveyed in an oil (DOWSIL EL 9241 DM) | 25 | 25 |
| Silicone oil (DIMETHICONE 100 CS) | 7.8 | 7.8 |
| Lecithin EMULMETIK 300 IP | 0.5 | 0.5 |
| UNIPURE RED LC | 0.9875 | 0.9875 |
| C 339001 SUN PURO | 2.48 | 2.48 |
| UNIPURE RED LC | 0.77 | 0.77 |
| SUNCROMA FDC YELLOW 6 AL LAKE | 4.8 | 4.8 |
| SUNCROMA FDC YELLOW 5 AL LAKE | 2.6 | 2.6 |
| UNIPURE RED LC | 5.55 | 5.55 |
| Hydrogenated polydecene DEKANEX 2006 FG (non-polar oil) | QS 100 | QS 100 |
| Polyethylene wax PERFORMALENE 500 (non-polar wax) | 7.45 | 5.2 |
| Candelilla wax CANDELILLA WAX SR 3 (polar wax) | — | 2.5 |
| Silica SUNSPHERE H33 | 3 | 3 |
| Silica SILICA SHELLS | 2 | 2 |
| Cross-linked silicone elastomer powder (DIMETHICONE/VINYL DIMETHICONE CROSSPOLYMER-DOW CORNING 9506 POWDER) | 6.5 | 6.5 |
| Silicone elastomer powder coated with silicone resin (KSP-100) | 3 | 3 |
| Calcium carbonate | 0.05 | 0.05 |
| Shea butter | 1.5 | 1.5 |

The compositions are prepared according to the following protocol:

the silicone elastomer conveyed in an oil (Dowsil 9241 EL) and Dimethicone 100cs are mixed under stirring at 95° C.; when the mixture is homogeneous, the polyethylene and candelilla waxes are incorporated;

the pigmentary paste comprising the pigments, hydrogenated polydecene and lecithin is added to the mixture prepared above when the waxes are melted, then the powders are sprinkled (fillers: silica shells, sunsphere H33, Dow Corning 9506 Powder and KSP 100) under stirring;

the mixture at a temperature greater than 95° C. is poured into a mould.

The lipsticks are evaluated for several criteria:

Organoleptic properties: sensory properties, colour: the compositions are tested for their properties of comfort, mattness and coverage.

Physicochemical properties: hardness, breakage test: the physicochemical measurements ensure the possible shaping of the composition of the invention, the strength of the stick during application and its breakage. In practice, the sticks are placed at 20° C. for 24 h. They are then cut at 1 cm from the cup using a wire in order to measure the hardness of the stick. The operation is carried out three times in order to produce an average. The hardness makes it possible to predict the behaviour of the stick on release from the mould, on breaking and during application. A texture analyser is used for the hardness measurement, the TAXT Plus and the Exponent software. The value obtained, expressed in grams force (Gf), must be between 140 and 190.

Stability: the formulas are monitored in various ovens in order to reproduce the life of the product. These accelerated ageing tests make it possible to ensure that the product is stable over time. The durability of the product can also be confirmed under normal conditions of storage and use. In practice, the stability of the sticks is observed after passage through various ovens: humidity, alternation between 4° C. and 45° C. The parts are stabilised 24 hours after their manufacture. The samples are observed after a defined time in each oven, 24 hours, 2 weeks, 1 month, 3 months. The absence of colour drift is observed, as well as the absence of drops, exudation and changes in the appearance of the stick: glossiness, mattness.

The composition of the invention makes it possible to obtain a matt stick with high coverage, having a rather "rigid" structure in order to have an unguided and comfortable structure (no tightness over time).

Example 3: Composition for Lips with Velvety Matt Effect

TABLE 3

| Ingredients | % |
| --- | --- |
| Hydrogenated polydecene | QS 100 |
| Cross-linked silicone elastomer conveyed in an oil (DIMETHICONE/DIMETHICONE CROSSPOLYMER-DOWSIL EL 9241 DM) | 25.0 |
| Dimethicone 100cs | 8.0 |
| Polyethylene wax | 5.5 |
| Cross-linked silicone elastomer powder (DIMETHICONE/VINYL DIMETHICONE CROSSPOLYMER-DOW | 3.0 |

TABLE 3-continued

| Ingredients | % |
| --- | --- |
| CORNING 9506 POWDER) | |
| Octyldodecanol | 5.2 |
| Candelilla wax | 3:25 |
| Cross-linked silicone elastomer powder coated with silicone resin (vinyl dimethicone/methicone silsesquioxane crosspolymer, KSP-100) | 3.0 |
| Pigments | 3.0 |
| Silica | 5.0 |
| Preservatives | QS |

The composition is stable. After application on the lips, a comfortable deposit is obtained, which is matt and non-desiccating, with a velvety appearance.

Example 4: Composition for Lips with Velvety Matt Effect

TABLE 4

| Ingredients | % |
| --- | --- |
| Hydrogenated polydecene | QS 100 |
| Cross-linked silicone elastomer conveyed in an oil (DIMETHICONE/DIMETHICONE CROSSPOLYMER-DOWSIL EL 9241 DM) | 25.0 |
| Dimethicone 100cs | 8.0 |
| Polyethylene wax | 5.5 |
| Cross-linked silicone elastomer powder (DIMETHICONE/VINYL DIMETHICONE CROSSPOLYMER-DOW CORNING 9506 POWDER) | 3.0 |
| Octyldodecanol | 5.2 |
| Candelilla wax | 3:25 |
| Cross-linked silicone elastomer powder coated with silicone resin (vinyl dimethicone/methicone silsesquioxane crosspolymer, KSP-100) | 6.5 |
| Pigments | 3.0 |
| Silica | 5.0 |
| Preservatives | QS |

The composition is stable. After application on the lips, a comfortable deposit is obtained, which is matt and non-desiccating, with a velvety appearance.

The invention claimed is:

1. A solid anhydrous cosmetic composition, comprising, in a physiologically acceptable medium, at least:

at least an organopolysiloxane elastomer conveyed in a first oil and an organopolysiloxane elastomer powder distinct from the organopolysiloxane elastomer conveyed in the first oil, a non-polar oil distinct from the first oil, one or more polar wax(es), the total content of organopolysiloxane elastomer active ingredient being greater than or equal to 7% relative to the total weight of said composition and the total content of wax(es) being greater than or equal to 5% by weight relative to the total weight of said composition, wherein the organopolysiloxane elastomer conveyed in a first oil has INCI name DIMETHICONE/DIMETHICONE CROSSPOLYMER and is present in a content of dry matter ranging from 1 to 8% by weight relative to the total weight of the composition and the organopolysiloxane elastomer powder distinct from the organopolysiloxane elastomer conveyed in the first oil is chosen from an organopolysiloxane elastomer powder coated with silicon resin with INCI name VINYL DIMETHICONE/METHICONE SILSESQUI-OXANE CROSSPOLYMER, an organopolysiloxane elastomer powder non-coated with silicon resin with INCI name DIMETHICONE/VINYL DIMETHI-CONE CROSSPOLYMER, and mixture thereof, in a total content ranging from 5 to 15% by weight relative to the total weight of the composition.

2. The composition according to claim 1, wherein the organopolysiloxane elastomer powder is coated with silicone resin.

3. The cosmetic composition according to claim 1, wherein the polar wax is selected from the group consisting of candelilla wax, beeswax, carnauba wax, rice bran wax, sunflower wax, jojoba wax, and the mixtures thereof.

4. The cosmetic composition according to claim 3, wherein the polar wax is a candelilla wax.

5. The cosmetic composition according to claim 1, further comprising at least one non-polar wax.

6. The cosmetic composition according to claim 1, further comprising at least one polar oil.

7. The cosmetic composition according to claim 1, further comprising coloring materials.

8. The cosmetic composition according to claim 1, wherein the composition is a lipstick, a lip contour pencil, or a lip balm.

9. A cosmetic method for care and/or make-up of the lips comprising applying, on the lips, the composition as defined in claim 1.

* * * * *